(12) United States Patent
Lorenz et al.

(10) Patent No.: US 6,384,216 B1
(45) Date of Patent: May 7, 2002

(54) PURIFICATION OF ALKENYL COMPOUNDS

(75) Inventors: Rudolf Erich Lorenz, Ludwigshafen; Arnd Böttcher, Frankenthal; Rolf Pinkos, Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/924,475

(22) Filed: Aug. 9, 2001

(30) Foreign Application Priority Data

Aug. 9, 2000 (DE) .......................... 100 38 747

(51) Int. Cl.⁷ .................. C07C 209/84; C07C 319/28; C07C 43/16; C07D 201/16; C07D 233/58
(52) U.S. Cl. .................. 540/540; 548/335.1; 564/437; 564/497; 568/57; 568/616; 568/621
(58) Field of Search ................ 540/540; 548/335.1; 564/437, 497; 568/57, 616, 621

(56) References Cited

U.S. PATENT DOCUMENTS 6,207,824 B1 * 3/2001 Henkes et al. .............. 540/451

OTHER PUBLICATIONS

Database CAPLUS on STN, Acc. No. 1973:505599, Kononov et al., 'Chromatographically pure N–vinylcaprolactam.' Dokl. Vses. Konf. Khim. Atsetilena, 4th (1973), vol. 3. pp. 18–22 (abstract).*
Database CAPLUS on STN, Acc. No. 1998:108098, Yoshii et al., 'Preparation of high–purity triethylene glycol divinyl ether.' JP10045653 (abstract).*
Ullmann's Encyclopedia of Ind. Chem, 6th Ed., 1999 Electronic Release, Chapter Vinyl Ethers.
Liebigs Ann. Chem. Bd. 601, 1956, Reppe et al. 81–138.

* cited by examiner

Primary Examiner—Brian J. Davis
(74) Attorney, Agent, or Firm—Keil & Weinkauf

(57) ABSTRACT

A process for purifying alkenyl compounds having a divalent or trivalent heteroatom in the α-position relative to the double bond by distillation comprises carrying out at least two distillations in which the purified alkenyl compounds are obtained from the gas phase by condensation, where the time between the first distillation after the synthesis of the alkenyl compounds and at least one further distillation is at least one day and the purified alkenyl compounds have an APHA color number of <30.

9 Claims, No Drawings

PURIFICATION OF ALKENYL COMPOUNDS

The present invention relates to a process for purifying alkenyl compounds having a divalent or trivalent heteroatom in the α position relative to the double bond, in particular alkenyl compounds of the formula (Ia) or (Ib)

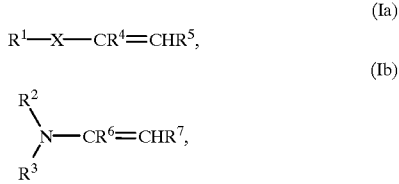

where X is a divalent heteroatom, $R^1$, $R^2$ and $R^3$ are each, independently of one another, a carbon-containing organic radical, where $R^2$ and $R^3$ may also be joined to one another, and $R^4$, $R^5$, $R^6$ and $R^7$ are each, independently of one another, hydrogen or a hydrocarbon radical, by distillation.

Alkenyl compounds are used, inter alia, as monomeric building blocks for oligomers, polymers and copolymers. Thus, alkenyl compounds are employed, for example, in the production of paper coatings, adhesives, printing inks, laundry detergents, motor oil additives, textile assistants, radiation-curing surface coatings, cosmetics, pharmaceuticals, auxiliaries for crude oil recovery or chemicals for photographic applications.

Alkenyl compounds are obtained industrially by means of various processes, for example by addition of alkynes (alkenylation), transfer of alkenyl groups, elimination to form the double bond or oxidative addition of alkenes. An overview of the preparation of vinyl ethers and vinyl esters is given in Ullmann's Encyclopedia of Industrial Chemistry, 6th edition, 1999 Electronic Release, Chapter "VINYL ETHERS" and Chapter "VINYL ESTERS".

W. Reppe et al., Justus Liebigs Ann. Chem., Vol. 601, 1956, pages 81 to 138, describe the preparation of vinyl ethers, vinyl esters, vinyl amines, vinyl-N-heterocycles and vinyl amides by, reaction of ethyne with the corresponding alcohols, carboxylic acids, amines, NH-heterocycles and amides in the presence of basic catalysts.

As indicated in the documents cited, the actual synthesis step is usually followed by purification by distillation, in which the desired products can be obtained in high purity by condensation from the gas phase. In this way, purities of significantly above 99% can be achieved without problems for very many alkenyl compounds, which is completely satisfactory for many applications.

However, in applications in which the products should have as little color as possible, for example in the cosmetic or photographic areas or in the case of paper coatings, it is not only a high chemical purity of the alkenyl compounds but also a very high purity in respect of color-imparting impurities which is demanded. Amounts of only a few ppm by weight of color-imparting impurities are generally sufficient to cause significant discoloration of the product.

As a measure of the color of transparent compounds, it is usual to report the APHA color number which is defined in DIN EN 1557 (March 1997). The lower the APHA color number, the more colorless is the product.

In the industrially customary distillation of alkenyl compounds immediately after their preparation, it is, depending on the type of alkenyl compounds and the color-imparting impurities present therein, impossible or possible only with great difficulty (e.g. large number of theoretical plates, high reflux ratio, additional purification steps such as adsorptive processes) to bring the APHA color number to below 40.

It is an object of the present invention to find a process for purifying alkenyl compounds which no longer has the abovementioned disadvantages and leads, without incurring high costs, to purified alkenyl compounds having a very low color number.

We have found that this object is achieved by a process for purifying alkenyl compounds having a divalent or trivalent heteroatom in the α-position relative to the double bond by distillation, which comprises carrying out at least two distillations in which the purified alkenyl compounds are obtained from the gas phase by condensation, where the time between the first distillation after the synthesis of the alkenyl compounds and at least one further distillation is at least one day and the purified alkenyl compounds have an APHA color number of <30.

For the purposes of the present invention, the term distillation encompasses quite generally all processes in which the alkenyl compounds are obtained from the gas phase by condensation. In general, the distillation is carried out in a distillation column having distillation packing and/or distillation trays as column internals. Examples of suitable column internals are ordered packing, random packing elements, valve trays, sieve trays and bubble cap trays. Preference is given to column internals which lead to a low pressure drop, for instance ordered packing and random packing elements. The second distillation and any further distillations are very particularly preferably carried out without column internals. The vaporization of the alkenyl compounds to be purified can in principle be achieved by a variety of constructions. Preference is given to using falling film and thin film evaporators, since these make particularly gentle vaporization possible. The purified alkenyl compounds are preferably isolated at the top.

The distillations in the process of the present invention can be carried out with or without reflux.

In the first distillation after the synthesis of the alkenyl compound, the alkenyl compound is separated from the by-products formed. To enable the separation task to be achieved reliably, it is preferably carried out with reflux. In this way, a purity of the alkenyl compound of over 99% can generally be achieved in the first distillation after the synthesis of the alkenyl compound.

Since the alkenyl compounds to be purified generally have a purity of significantly above 99% before the second distillation and any further distillations and the traces of color-imparting impurities to be removed preferably remain in the bottoms, the second distillation and any further distillations are preferably carried out without reflux. The absence of reflux brings with it a series of economic advantages, for example simpler construction of the apparatus, a lower instrumentation requirement and a lower energy and time requirement.

The distillations in the process of the present invention can be carried out batchwise, semicontinuously or continuously. In the case of batchwise distillation, the alkenyl compound to be purified is generally introduced all at once into the still pot and is vaporized by heating and/or lowering the pressure. The distilled, purified alkenyl compound is taken off continuously or passed to a receiver. A semicontinuous distillation is generally commenced in a manner similar to the batchwise distillation, but the still pot is refilled during the distillation process. In the case of a continuous distillation, the alkenyl compound to be purified is fed continuously into the distillation apparatus and the distilled, purified product is taken off continuously.

The distillations in the process of the present invention can in principle be carried out at atmospheric pressure, at subatmospheric pressure (e.g. as a vacuum distillation) or at superatmospheric pressure. The choice of the pressure and thus the distillation temperature generally depends on the product to be distilled and the impurities present therein. Preference is given to carrying out both the first distillation after the synthesis of the alkenyl compounds and the second and any further distillations under a pressure lower than or equal to atmospheric pressure, particularly preferably at subatmospheric pressure.

An essential aspect of the process of the present invention is that the time between the first distillation after the synthesis of the alkenyl compounds and at least one further distillation is at least one day. In each case, the distillation is considered to be complete at the time at which the alkenyl compounds have been condensed from the gas phase and isolated. In general, the condensed, purified alkenyl compounds are isolated by being passed to a receiver.

In general, a total of two distillations are sufficient for achieving the desired APHA color number of <30 in the process of the present invention. The first distillation is generally carried out immediately after the synthesis of the alkenyl compounds and the second distillation is carried out after expiry of the specified time, namely at least one day. However, it is also possible to carry out further distillations.

Furthermore, it has surprisingly been found that the purified alkenyl compounds obtainable by means of the process of the present invention have a lower color number the greater the time between the first distillation after the synthesis and at least one further distillation. In the process of the present invention, this time is at least one day. It is preferably at least 2 days, particularly preferably at least 5 days and very particularly preferably at least 10 days.

It may be advantageous to add a stabilizer before or during storage. The type and amount of stabilizer generally depends on the type of alkenyl compound and is known by or can routinely be determined by a person skilled in the art. A widely applicable and very frequently used stabilizer is, for example, N,N'-bis(1-methylpropyl)-1,4-phenylenediamine, which is marketed by BASF AG under the tradename Kerobit® BPD. A further frequently used stabilizer is, for example, potassium hydroxide.

The storage conditions are generally not critical, i.e. the storage can in principle be carried out under various conditions. Since the alkenyl compounds are generally reactive compounds, it is advantageous to choose gentle conditions. Storage is therefore advantageously carried out at below 40° C., preferably below 30° C., possibly under a protective gas atmosphere. Alkenyl compounds which are solid under these conditions are generally stored in the solid state and are melted prior to the distillation. For the present purposes, the term storage encompasses transport such as pumping through a pipe or transportation in a container.

After the process of the present invention has been carried out, the purified alkenyl compounds have an APHA color number of <30. The definition and determination of the APHA color number are described in DIN EN 1557 (March 1997). The purified alkenyl compounds obtained after carrying out the process of the present invention preferably have an APHA color number of ≦20, particularly preferably ≦10. Thus, alkenyl compounds having an APHA color number of significantly below 10 can generally be obtained without problems after a storage time of only a few days.

The alkenyl compounds to be purified in the process of the present invention have, for example, the formula (Ia) or (Ib)

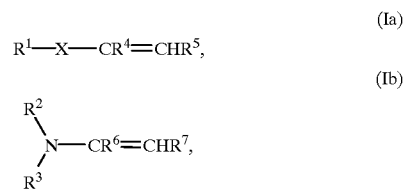

where X is a divalent heteroatom, $R^1$, $R^2$ and $R^3$ are each, independently of one another, a carbon-containing organic radical, where $R^2$ and $R^3$ may also be joined to one another, and $R^4$, $R^5$, $R^6$ and $R^7$ are each, independently of one another, hydrogen or a hydrocarbon radical.

For the purposes of the present invention, a carbon-containing organic radical is an unsubstituted or substituted, aliphatic, aromatic or araliphatic radical having from 1 to 22 carbon atoms. This radical may contain one or more heteroatoms such as oxygen, nitrogen or sulfur, for example —O—, —S—, —NR—, —CO— and/or —N= in aliphatic or aromatic systems, and/or may be substituted by one or more functional groups containing, for example, oxygen, nitrogen, sulfur and/or halogen, for example by fluorine, chlorine, bromine, iodine and/or a cyano group. If the carbon-containing-organic radical contains one or more heteroatoms, it can also be bound via a heteroatom or a heteroatom-bearing carbon atom. Thus, for example, radicals which are bound via a nitrogen atom or a carbon group are also included.

Preferred monovalent, i.e. terminal, carbon-containing organic radicals $R^1$, $R^2$ or $R^3$ are:
  unbranched or branched, acyclic or cyclic alkyl having from 1 to 22 aliphatic carbon atoms, in which one or more of the —CH$_2$— groups may also be replaced by heteroatoms such as —O—, or by heteroatom-containing groups such as —CO— or —NR— and in which one or more of the hydrogen atoms may be replaced by substituents, for example aryl groups,
  unbranched or branched, acyclic or cyclic alkenyl having from 2 to 22 aliphatic carbon atoms and one or more double bonds in any positions, in which one or more of the —CH$_2$— groups may also be replaced by heteroatoms such as —O—, or by heteroatom-containing groups such as —CO— or —NR— and in which one or more of the hydrogen atoms may be replaced by substituents, for example aryl groups,
  aryl having up to 10 aromatic carbon atoms, in which one or more of the =CH— groups may be replaced by heteroatoms such as =N— and in which one or more of the hydrogen atoms may be replaced by substituents, for example alkyl groups,
  and radicals as mentioned above in which one or more of the hydrogen atoms are replaced by a X—CR4=CHR5 or >Y—CR6=CHR7—group.

Preferred divalent organic radicals formed by $R^2$—$R^3$ are:
  unbranched or branched alkylene having from 3 to 20 aliphatic carbon atoms, in which one or more of the —CH$_2$— groups may also be replaced by heteroatoms such as —O—, or by heteroatom-containing groups such as —CO— or —NR— and in which one or more of the hydrogen atoms may be replaced by substituents, for example aryl groups,
  unbranched or branched alkenylene having from 3 to 20 carbon atoms and one or more double bonds, in which one or more of the —CH$_2$— groups may also be replaced by heteroatoms such as —O— or by heteroatom-containing groups such as —CO— or —NR— in which one or more of the =CH— groups may also be replaced by heteroatoms such as =N— and in which one or more of the hydrogen atoms may be replaced by substituents, for example aryl groups.

The divalent heteroatom X in the alkenyl compounds (Ia) can be an oxygen atom or a sulfur atom. Examples of alkenyl compounds (Ia) are alkenyl ethers, alkenyl esters and alkenyl sulfides. The process of the present invention is preferably carried out using alkenyl compounds (Ia) in which X is oxygen.

Examples of alkenyl compounds (Ib) are alkenylamines, N-alkenylamides and N-alkenylheterocycles. The term N-alkenylamides also encompasses cyclic N-alkenylamides, which are also known as N-alkenyllactams.

For the purposes of the present invention a hydrocarbon radical is an aliphatic, aromatic or araliphatic radical having from 1 to 12 carbon atoms. Preferred hydrocarbon radicals $R^4$, $R^5$, $R^6$ and $R^7$ are $C_1$–$C_4$-alkyl, for example methyl, ethyl, 1-propyl, 2-propyl, 1-butyl, 2-butyl, 2-methyl-1-propyl and 2-methyl-2-propyl, in particular methyl, $C_6$-aryl, specifically phenyl, $C_7$–$C_8$-aralkyl, for example phenylmethyl and phenylethyl, and $C_7$–$C_8$-alkaryl, for example 2-methylphenyl, 3-methylphenyl and 4-methylphenyl.

Particular preference is given to alkenyl compounds (Ia) and (Ib), in which the radicals $R^4$, $R^5$, $R^6$ and $R^7$ are each, independently of one another, hydrogen or methyl. Very particular preference is given to alkenyl compounds (Ia) and (Ib) in which the radicals $R^4$, $R^5$, $R^6$ and $R^7$ are hydrogen, i.e. the vinyl compounds.

Examples of alkenyl sulfides of the formula (Ia) with X=sulfur which can be used in the process of the present invention are vinyl methyl sulfide, vinyl ethyl sulfide, vinyl 1-propyl sulfide, vinyl 2-propyl sulfide (vinyl isopropyl sulfide), vinyl 1-butyl sulfide, vinyl 2-butyl sulfide (vinyl sec-butyl sulfide), vinyl (2-methyl-2-propyl) sulfide (vinyl tert-butyl sulfide), vinyl pentyl sulfide and its isomers and vinyl hexyl sulfide and its isomers.

The alkenyl compounds (Ia) used in the process of the present invention are particularly preferably vinyl ethers. Examples of preferred vinyl ethers are vinyl methyl ether, vinyl ethyl ether, vinyl 1-propyl ether, vinyl 2-propyl ether (vinyl isopropyl ether), vinyl 1-butyl ether, vinyl 2-butyl ether (vinyl sec-butyl ether), vinyl 2-methyl-2-propyl ether (vinyl tert-butyl ether), vinyl pentyl ether and its isomers, vinyl hexyl ether and its isomers, vinyl heptyl ether and its isomers, vinyl octyl ether and its isomers, vinyl nonyl ether and its isomers, vinyl decyl ether and its isomers, vinyl undecyl ether and its isomers, vinyl dodecyl ether and its isomers, vinyl tridecyl ether and its isomers, vinyl tetradecyl ether and its isomers, vinyl pentadecyl ether and its isomers, vinyl hexadecyl ether and its isomers, vinyl heptadecyl ether and its isomers, vinyl octadecyl ether and its isomers, vinyl nonadecyl ether and its isomers, vinyl eicosyl ether and its isomers, vinyl henicosyl ether and its isomers, vinyl docosyl ether and its isomers, vinyl cyclopentyl ether, vinyl cyclohexyl ether, vinyl cycloheptyl ether, vinyl cyclooctyl ether, vinyl cyclododecyl ether, vinyl phenyl ether, vinyl 2-methylphenyl ether, vinyl 3-methyl-phenyl ether, vinyl 4-methylphenyl ether, vinyl phenylmethyl ether, vinyl 2-phenylethyl ether, 2-hydroxyethyl vinyl ether (3-oxapent-4-en-1-ol), ethylene glycol divinyl ether (3,6-dioxaocta-1,7-diene), diethylene glycol monovinyl ether (3,6-dioxaocta-7-en-1-ol), diethylene glycol divinyl ether (3,6,9-trioxaundeca-1,10-diene), triethylene glycol monovinyl ether (3,6,9-trioxaundeca-10-en-1-ol), triethylene glycol divinyl ether (3,6,9,12-tetraoxatetradeca-1,13-diene), tetraethylene glycol monovinyl ether (3,6,9,12-tetraoxatetradeca-13-en-1-ol), tetraethylene glycol divinyl ether (3,6,9,12,15-pentaoxaheptadeca-1,16-diene), 1,2-propylene glycol monovinyl ether (4-oxahexa-5-en-2-ol and 2-methyl-3-oxapent-4-en-1-ol), 1,2-propylene glycol divinyl ether (4-methyl-3,6-dioxaocta-1,7-diene), 3-hydroxypropyl vinyl ether (5-oxa-hept-6-en-1-ol), 1,3-propylene glycol divinyl ether (3,7-dioxanona-1,8-diene), 4-hydroxybutyl vinyl ether (5-oxahept-6-en-1-ol), 1,4-butylene glycol divinyl ether (3,8-dioxadeca-1,9-diene), 5-hydroxypentyl vinyl ether (6-oxaoct-7-en-1-ol), 1,5-pentylene glycol divinyl ether (3,9-dioxaundeca-1,10-diene), 6-hydroxyhexyl vinyl ether (7-oxanon-8-en-1-ol), 1,6-hexylene glycol divinyl ether (3,10-dioxadodeca-1,11-diene), 8-hydroxyoctyl vinyl ether (9-oxaundec-10-en-1-ol), 1,8-octylene glycol divinyl ether (3,12-dioxatetradeca-1,13-diene), 12-hydroxydodecyl vinylether (13-oxapentadec-14-en-1-ol), 1,12-dodecylene glycol divinyl ether (3,16-dioxaoctadeca-1,17-diene), 4-hydroxycyclohexyl vinyl ether, 1,4-cyclohexylene divinyl ether (1,4-bis(vinyloxy)cyclohexane), 4-vinyloxyphenol and bis(vinyloxy)-1,4-phenylene.

Vinyl ethers which are very particularly preferred in the process of the present invention are ethylene glycol divinyl ether (3,6-dioxaocta-1,7-diene), diethylene glycol divinyl ether (3,6,9-trioxaundeca-1,10-diene), triethylene glycol divinyl ether (3,6,9,12-tetraoxatetradeca-1,13-diene) and 4-hydroxybutyl vinyl ether (5-oxahept-6-en-1-ol).

Alkenyl compounds (Ib) used in the process of the present invention are particularly preferably acyclic and cyclic N-vinyl amines, acyclic and cyclic N-vinyl amides and N-vinyl heterocycles, in particular N-vinyl amides and N-vinyl heterocycles.

Examples of preferred acyclic and cyclic N-vinyl amines are N-vinyldimethylamine, N-vinyldiethylamine, N-vinyldi(1-propyl)amine, N-vinyldi(2-propyl)amine (N-vinyldiisopropylamine), N-vinyldi(1-butyl)amine, N-vinyldi(2-butyl)amine (N-vinyldi-sec-butylamine), N-vinyldi(2-methyl-2-propyl)amine (N-vinyldi-tert-butylamine), N-vinylmethylethylamine, N-vinylmethyl(1-propyl)amine, N-vinylmethyl(2-propyl)amine (N-vinylmethylisopropylamine), N-vinylmethyl(1-butyl)amine, N-vinylmethyl(2-butyl)amine (N-vinylmethylsec-butylamine), N-vinylmethyl(2-methyl-2-propyl)amine (N-vinylmethyl-tert-butylamine), N-vinylmethylpentylamine and its isomers, N-vinylmethylhexylamine and its isomers, N-vinylmethylheptylamine and its isomers, N-vinylmethyloctylamine and its isomers, N-vinylmethylnonylamine and its isomers, N-vinylmethyldecylamine and its isomers, N-vinylmethylundecylamine and its isomers, N-vinylmethyldodecylamine and its isomers, N-vinylmethyltridecylamine and its isomers, N-vinylmethyltetradecylamine and its isomers, N-vinylmethylpentadecylamine and its isomers, N-vinylmethylhexadecylamine and its isomers, N-vinylmethylheptadecylamine and its isomers, N-vinylmethyloctadecylamine and its isomers, N-vinylmethylnonadecylamine and its isomers, N-vinylmethyleicosylamine and its isomers, N-vinylmethylhenicosylamine and its isomers, N-vinylmethyldocosylamine and its isomers, N-vinylmethylcyclopentylamine, N-vinylmethylcyclohexylamine, N-vinylmethylcycloheptylamine, N-vinylmethylcyclooctylamine, N-vinylmethylcyclododecylamine, N-vinylmethylphenylamine, N-vinyldiphenylamine, N-vinylmethyl(2-methylphenyl)amine, N-vinylmethyl(3-methylphenyl)amine, N-vinylmethyl(4-methylphenyl)amine, N-vinylmethyl(phenylmethyl)amine, N-vinylmethyl(2-phenylethyl)amine, N-vinylpyrrolidine, N-vinylpiperidine, N-vinylmorpholine.

Examples of preferred acyclic and cyclic N-vinyl amides are N-vinyl-N-methylacetamide, N-vinylpyrrolidone, N-vinyl-2-piperidone (N-vinyl-δ-valerolactam), N-vinyl-ε-caprolactam (N-vinyl lactam of 6-aminohexanoic acid), the N-vinyl lactam of 7-aminoheptanoic acid, the N-vinyl lactam of 8-aminooctanoic acid, the N-vinyl lactam of 9-aminononanoic acid, the N-vinyl lactam of 10-aminodecanoic acid, the N-vinyl lactam of 12-aminododecanoic acid (N-vinyllaurolactam).

N-vinyl amides which are very particularly preferred in the process of the present invention are N-vinyl-2-piperidone (N-vinyl-δ-valerolactam) and N-vinyl-ε-caprolactam (N-vinyl lactam of 6-aminohexanoic acid).

Examples of preferred N-vinyl heterocycles are N-vinylpyrrole, N-vinylpyrazole, N-vinylimidazole, N-vinyl-1,2,3-triazole, N-vinyl-1,2,4-triazole, N-vinyl-1,3,4-triazole and N-vinyl-2-methylimidazole.

The very particularly preferred N-vinyl heterocycle in the process of the present invention is N-vinylimidazole.

In a preferred embodiment of the process of the present invention, the alkenyl compound originating from the preceding synthetic step, including work-up of the crude product by distillation, is stored for at least one day at below 40° C. and is subsequently subjected to a further distillation to achieve the desired APHA color number.

This storage can be carried out in many ways. In a preferred variant, the alkenyl compound which has been distilled after the synthesis is stored in an intermediate vessel (e.g. a drum, a container or a tank), taken out after one day at the earliest and redistilled as described to achieve the desired APHA color number.

In another preferred variant, the alkenyl compound distilled after synthesis is firstly, if desired, stored in an intermediate vessel (e.g. a drum, a container or a tank), subsequently transported in a suitable vessel (e.g. a drum, a container or a tank), subsequently, if desired, stored again in an intermediate vessel (e.g. a drum, a container or a tank) and subsequently, but at the earliest after one day calculated from the first distillation after the synthesis, taken out and distilled as described to achieve the desired APHA color number.

The purification process of the present invention for purifying alkenyl compounds by distillation leads to a purified product having a very low color number. The process of the present invention can be carried out very efficiently and economically at low cost. As a result of the second and possibly further distillations which are simple to carry out industrially and can preferably even be carried out without reflux, the process of the present invention has a low energy consumption and low demands in terms of materials. The yield of the purified alkenyl compounds is very high, frequently even almost quantitative. The process of the present invention is successful in the case of both unstabilized and stabilized alkenyl compounds. Alkenyl compounds having an APHA color number of significantly below 10 can be obtained without problems by means of the process of the present invention.

EXAMPLES

Examples 1 and 2

N-Vinyl-ε-caprolactam was obtained by base-catalyzed reaction of ε-caprolactam with ethyne and the crude product was subsequently distilled. The N-vinyl-ε-caprolactam obtained comprised 99.7 GC-% by area of N-vinyl-ε-caprolactam and 0.25 GC-% by area of unreacted ε-caprolactam. The APHA color number was 55.

In Example 1 (comparative example), the N-vinyl-ε-caprolactam obtained was immediately, i.e. without intermediate storage, redistilled in a downstream column at a pressure of about 0.6 kPa abs at the top and a temperature at the bottom of about 130° C. The distillation column was provided with a random packing and was operated at a reflux ratio of 1. The purified N-vinyl-ε-caprolactam obtained via the top had an APHA color number of 30.

In Example 2 (according to the present invention), the N-vinyl-ε-caprolactam obtained from the distillation of the crude product in Example 1 was stored without addition of a stabilizer for 5 days at about 25° C. The APHA color number rose to 100. It was subsequently redistilled from a still pot, i.e. without a column, at about 0.7 kPa abs and a liquid-phase temperature of about 126° C. The purified N-vinyl-ε-caprolactam obtained via the top had an APHA color number of only 5.

Example 3

According to the Present Invention

N-vinylimidazole was obtained by base-catalyzed reaction of imidazole with ethyne and distilled. The N-vinylimidazole obtained had an APHA color number of 50. After storage for 2 days at 25° C., the unstabilized N-vinylimidazole was redistilled from the still pot of the same apparatus as in Example 2 at about 0.5 kPa abs. The purified N-vinylimidazole obtained via the top had an APHA color number of only 3.

Example 4

According to the Present Invention

Diethylene glycol divinyl ether was obtained by base-catalyzed reaction of diethylene glycol with ethyne and distilled. The diethylene glycol divinyl ether obtained was stabilized with 100 ppm by weight of potassium hydroxide and had an APHA color number of 45. After storage for 5 days at 25° C., the diethylene glycol divinyl ether was redistilled from the still pot of the same apparatus as in Example 2 at about 0.5 kPa abs. The purified diethylene glycol divinyl ether obtained via the top had an APHA color number of only 3.

Example 5

According to the Present Invention

Triethylene glycol divinyl ether was obtained by base-catalyzed reaction of triethylene glycol with ethyne and distilled. The triethylene glycol divinyl ether obtained was stabilized with 100 ppm by weight of potassium hydroxide and had an APHA color number of 105. After storage for 30 days at 25° C., the triethylene glycol divinyl ether was redistilled from the still pot of the same apparatus as in Example 2 at about 0.5 kPa abs. The purified triethylene glycol divinyl ether obtained via the top had an APHA color number of only 5.

Table 1 gives a summary of the results.

| Example | Product | Storage time [days] | APHA color number before distillation | APHA color number after distillation |
|---|---|---|---|---|
| 1* | N-vinyl-ε-caprolactam | none | 55 | 30 |
| 2 | N-vinyl-ε-caprolactam | 5 | 55 | 5 |
| 3 | N-vinylimidazole | 2 | 50 | 3 |
| 4 | Diethylene glycol divinyl ether | 5 | 45 | 3 |
| 5 | Triethylene glycol divinyl ether | 30 | 105 | 5 |

*Comparative experiment

The examples show that APHA color numbers of significantly below, 30 can be obtained without problems and in a simple way for the various vinyl compounds by means of the process of the present invention.

As comparative example 1 and Example 2 according to the present invention show, this is made possible only by an appropriate storage time between the first distillation after the synthesis of the alkenyl compound and the second or possibly further distillation.

We claim:

1. A process for purifying alkenyl compounds having a divalent or trivalent heteroatom in the α position relative to the double bond by distillation, which comprises carrying out at least two distillations in which the purified alkenyl compounds are obtained from the gas phase by condensation, where the time between the first distillation after the synthesis of the alkenyl compounds and at least one further distillation is at least one day and the purified alkenyl compounds have an APHA color number of <30.

2. A process as claimed in claim 1, wherein the time between the first distillation after the synthesis of the alkenyl compounds and at least one further distillation is at least five days.

3. A process as claimed in claim 1, wherein the purified alkenyl compounds have an APHA color number of ≦10.

4. A process as claimed in claim 1, wherein the alkenyl compounds are compounds of the formula (Ia) or (Ib)

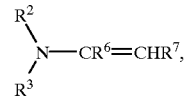

where X is a divalent heteroatom, $R^1$, $R^2$ and $R^3$ are each, independently of one another, a carbon-containing organic radical, where $R^2$ and $R^3$ may also be joined to one another, and $R^4$, $R^5$, $R^6$ and $R^7$ are each, independently of one another, hydrogen or a hydrocarbon radical.

5. A process as claimed in claim 1, wherein the alkenyl compounds are vinyl compounds.

6. A process for purifying alkenyl compounds (Ia) as claimed in claim 4 by distillation, wherein X is oxygen.

7. A process as claimed in claim 6, wherein the alkenyl compounds (Ia) are vinyl ethers.

8. A process as claimed in claim 4, wherein the alkenyl compounds (Ib) are N-vinyl amides or N-vinyl heterocycles.

9. A process as claimed in claim 8, wherein the alkenyl compound (Ib) is N-vinylimidazole or N-vinyl-ε-caprolactam.

* * * * *